United States Patent [19]

Valentine, Jr.

[11] 4,123,465

[45] Oct. 31, 1978

[54] CHIRAL TERTIARY PHOSPHINES

[75] Inventor: Donald H. Valentine, Jr., Westfield, N.J.

[73] Assignee: Hoffmann-La Roche Inc., Nutley, N.J.

[21] Appl. No.: 823,373

[22] Filed: Aug. 10, 1977

Related U.S. Application Data

[60] Division of Ser. No. 623,140, Oct. 16, 1975, abandoned, which is a continuation-in-part of Ser. No. 519,442, Oct. 31, 1974, abandoned.

[51] Int. Cl.$^2$ .............................................. C07F 9/50
[52] U.S. Cl. ..................... 260/606.5 P; 252/431 P; 260/409; 260/413
[58] Field of Search ................................ 260/606.5 P

[56] References Cited

U.S. PATENT DOCUMENTS

| | | | |
|---|---|---|---|
| 3,639,439 | 2/1972 | Dewhirst | 260/429 R |
| 3,759,838 | 9/1973 | Dewhirst | 252/429 R |
| 3,798,241 | 3/1974 | Kagan et al. | 260/340.9 |
| 3,849,480 | 11/1974 | Knowles et al. | 260/429 R X |
| 3,883,580 | 5/1975 | Solodar | 252/429 R X |
| 3,966,595 | 6/1976 | Gosser | 260/429 R |
| 3,968,147 | 7/1976 | Solodar | 252/431 P X |
| 4,008,281 | 2/1977 | Knowles et al. | 260/606.5 P |
| 4,010,181 | 3/1977 | Aviron-Violet | 260/690 X |

*Primary Examiner*—Helen M. S. Sneed
*Attorney, Agent, or Firm*—Samuel L. Welt; Bernard S. Leon; George W. Johnston

[57] ABSTRACT

A method for the homogeneous catalytic enantioselective hydrogenation of alkyl and alkenyl substituted acrylic acids wherein these acids are selectively hydrogenated at the double bond alpha,beta to the acid function, said hydrogenations are catalyzed by rhodium complexes of chiral tertiary phosphines. This method provides a route to chiral dihydrogeranic acid and other intermediates useful in the synthesis of chiral vitamin E, citronellal, and menthol. Novel chiral tertiary phosphines are also disclosed.

10 Claims, No Drawings

CHIRAL TERTIARY PHOSPHINES

This is a division, of application Ser. No. 623,140 filed Oct. 16, 1975 now abandoned, which is a continuation-in-part of Ser. No. 519,442, filed Oct. 31, 1974, now abandoned.

BACKGROUND OF THE INVENTION

Phosphine complexes of transition metals have been widely employed as soluble catalysts for hydrogenation of carbon to carbon double bonds. Particularly useful and widely studied have been phosphine complexes of rhodium (I) such as $Rh(PPh_3)_3Cl$, which was described in some detail by Wilkinson and co-workers, e.g., Osborne et al. *J. Chem. Soc. Sect. A,* 1711 (1966) and has since been very thoroughly studied. Detailed reviews of these topics have appeared (e.g. Harmon et al. *Chem. Reviews* 73, 21 (1973); B. R. James, *Homogeneous Hydrogenation*).

When the ($PPh_3$) moiety of the above-mentioned transition metal complex is replaced by a chiral tertiary phosphine, hydrogenation of a prochiral olefin leads to an excess of one enantiomer of the saturated hydrogenation product. Enantioselective hydrogenation of alpha- and beta-phenyl acrylic acids and alpha-acylamido-beta-phenyl acrylic acids employing chiral tertiary phosphines has been disclosed by Knowles et al. *Chem. Tech.* 590 (1972) and references therein; Morrison et al., *J. Amer. Chem. Soc.* 93, 1301 (1971); Kagan et al., *J. Amer. Chem. Soc.* 94, 6429 (1972) and references therein.

A typical example of such a catalyst is the rhodium (I) complex of neomenthyldiphenylphosphine (1S, 2S, 5R-1-diphenylphosphino-2-isopropyl-5-methyl cyclohexane) described by Morrison et al., supra. Further discussion of these topics may be found, e.g., in Scott and Valentine, *Science* 184, 943 (1974). In addition, two processes for the enantioselective hydrogenations of alpha-acylamido-beta-phenyl acrylic acids are disclosed and claimed in German Offenlegungschrifts Nos. 2,123,063 (Dec. 2, 1971) and 2,161,200 (June 22, 1972).

Other references pertaining to asymmetric hydrogenation are (1) Knowles et al., *J. Am. Chem. Soc.* 97, 2567 (1975) relating to asymmetric hydrogenation of substituted amino acids and α-phenyl acrylic acid; (2) Knowles et al. (appearing in Advan. Chem. Soc. 132, (1974) pp 274–282 where optically active amino acids are prepared by asymmetric hydrogenation employing a rhodium-chiral phosphine catalyst; (3) Solodar, U.S. Pat. No. 3,883,580 discloses the asymmetric reduction of ketones to form optically active secondary alcohol employing a Group VIII metal coordination complex catalyst; and (4) Knowles et al., U.S. Pat. No. 3,849,480 discloses and claims the selective hydrogenation of a substituted or unsubstituted olefin employing as catalyst a coordination complex of a metal. The reference does not disclose homogeneous enantioselective hydrogenations of acrylic acids within the scope of formulas II and III.

SUMMARY OF THE INVENTION

This invention relates to asymmetric hydrogenation of alkyl and alkenyl substituted acrylic acids. More specifically, the invention relates to homogeneous hydrogenations catalyzed by rhodium (I) complexes of chiral tertiary phosphines wherein the hydrogenation occurs enantioselectively resulting in an optically active aliphatic carboxylic acid.

In accordance with the invention $C_9$–$C_{15}$ optically active alkanoic monocarboxylic acids having the formula:

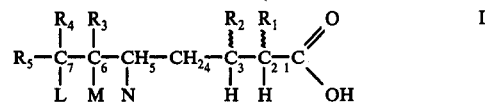

wherein at least one of $R_1$ and $R_2$ are lower alkyl and the other is hydrogen; $R_3$ and $R_4$ are hydrogen or lower alkyl; $R_5$ is hydrogen, lower alkyl or lower alkenyl; L, M, and N are hydrogen or may be taken together to form a carbon to carbon double bond; with the proviso that when L and M form a double bond, N is hydrogen or lower alkyl and when M and N form a double bond, L is hydrogen or lower alkyl; are prepared by the enantioselective hydrogenation of aliphatic acrylic acids having the formula:

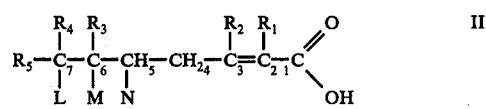

wherein $R_1$, $R_2$, $R_3$, $R_4$, $R_5$, L, M, and N are as defined above and the carbon to carbon double bond at the 2-position being predominately either cis or trans; or by the enantioselective hydrogenation of acrylic acids having the formula:

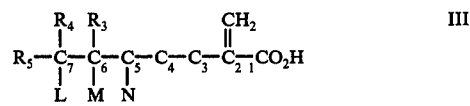

wherein $R_3$, $R_4$, $R_5$, L, M, and N are as defined above; which comprises hydrogenating said acrylic acid in the presence of a rhodium (I) complex of a chiral tertiary phosphine under basic conditions in a solvent media. The alkanoic monocarboxylic acids produced by the instant process are obtained as a mixture of enantiomers wherein there is an excess of either R- or S-enantiomer. The enantiomer in excess will be dictated by the chiral phosphine used and the isomeric form of the substrate, i.e., E or Z. The monocarboxylic acids herein produced have a high degree of optical activity.

The instant invention thus satisfies a long felt need by providing to the art a new route toward the preparation of dihydrogeranic acid and thus vitamin E precursors by the enantioselective hydrogenation of alkyl and alkenyl substituted acrylic acids as well as the production of certain of said acids having a high degree of optical purity.

DETAILED DESCRIPTION OF THE INVENTION

The term "chiral tertiary phosphine" as used herein denotes either a phosphine compound comprised of phosphorous having substituted thereon three different hydrocarbon radicals or a phosphine compound which has three hydrocarbon radical substituents, at least one of which is chiral.

The term "prochiral" as used herein refers to a carbon atom center having two like substituents, i.e., $CZ_2XY$, such that a change in one of said like substituents leads to a chiral carbon atom center, i.e., CWXYZ.

The term "lower alkyl" refers to an alkyl group having saturated aliphatic straight or branched chains of from 1-6 carbon atoms. Exemplary of the hydrocarbon groups contemplated are methyl, ethyl, propyl, isopropyl, 3-methyl butyl and the like.

The term "lower alkenyl" refers to alkenyl groups having unsaturated aliphatic straight or branched chains of from 1-6 carbon atoms. Exemplary of the hydrocarbon groups contemplated are vinyl, propenyl, butenyl, hexenyl, 3-methyl-but-2-enyl and the like.

The term "lower alkanols" refers to alcohols having saturated aliphatic straight or branched chains of 1-7 carbon atoms. Exemplary of the alcohols contemplated are methanol, ethanol, propanol, isopropanol and the like.

The term "enantioselective hydrogenation" as used herein, refers to the hydrogenation of a prochiral carbon-to-carbon double bond in such a way as to produce an excess of one enantiomer of the saturated product.

The term "optical purity" as used herein, refers to the optical rotation of an enantiomeric mixture prepared according to the invention divided by the optical rotation of a pure enantiomer which is used as a standard and expressed as a percent.

The term "enantiomeric excess" as used herein, refers to a numerical value, expressed in percent indicating the predominance of one enantiomer in relation to another, e.g., excess of the R-enantiomer expressed as percent of R-enantiomer minus percent of S-enantiomer.

The terms "R- and S-enantiomer" refer to the configuration of the substituents about the asymmetric carbon atom in optically active organic compounds as prescribed in standard IUPAC nomenclature.

The terms "entgegen" (E) and "zusammen" (Z) refer to the disposition of substituents about carbon to carbon double bonds as prescribed in standard IUPAC nomenclature.

In schematic representations of molecular structures, the wedges (▲) indicate that the substituent is above the plane of the molecule, the broken lines (--) indicate that the substituents are below the plane of the molecule, and the wavy lines (~) indicate that the substituents may be either above or below the plane of the molecule.

In accordance with the instant invention, the substrates are acrylic acid derivatives having only alkyl or alkenyl substituents. The acrylic acids contemplated herein are those having the formulas (II) and (III) above. Typical compounds of the formula (II) above falling within the scope of the instant invention are (2,6-dimethyl-hept-2-enoic acid), *entgegen* 3,7-dimethylocta-2,6-dienoic acid (geranic acid), *zusammen* 3,7-dimethylocta-2,6-dienoic acid (nerolic acid), 2,6,10-trimethylundeca-2,9-dienoic acid, 3,7,11-trimethyldodeca-2,6,10-trienoic acid and 3,7,11-trimethyldodec-2-enoic acid. Typical compounds of the formula (III) above falling within the scope of the instant invention are 2-methylene-6-methylheptanoic acid, 2-methylene-6-methylhept-6-enoic acid, 2-methylene-6-methylhept-5-enoic acid, 2-methylene-6R,10-dimethylundec-9-enoic acid and 2-methylene-6R,10-dimethylundecanoic acid.

The process described herein may be applied to E- or Z-isomers of the acids of formula (II) or mixtures thereof, to acrylic acid derivatives of formula (III) or to mixtures of the acids of formula (III) with acids of the formula (II). To obtain products containing a high enantiomeric excess, however, it is usually preferred to use a pure isomer or mixtures containing a predominance of one isomer.

Acids of formula (II) wherein $R_1 = CH_3$ and $R_2 = H$ are readily prepared by standard methods and are typically found to be more than 95% E-isomer. Acids of formula (III) are also readily prepared in high isomeric purity, e.g., by the acid catalyzed dehydration of 2-hydroxymethyl carboxylic acids. However, acids of formula (II) wherein $R^1 = H$ and $R_2 = CH_3$ or $—CH_2CH_3$ are typically obtained as a mixture of E- and Z-isomers. Prior to carrying out the hydrogenation process of this invention, it is desirable to obtain the E-isomer in enriched form (i.e., higher E/Z ratio). Separation of E- and Z-isomers of acids of formula (II) wherein $R^1 = H$ and $R^2 = CH_3$ can be accomplished by standard methods of separation, such as distillation.

It has unexpectedly been observed that the E-isomer component of E- and Z-isomer mixtures of acids of formula (II), wherein $R^1 = H$ and $R^2 = CH_3$ or $—CH_2CH_3$ can be recovered from these mixtures by crystallization from inert hydrocarbon or ether solvents at reduced temperature. Thus, if the isomer mixture of the aforementioned acid of formula (II) is dissolved in 1-50 parts of hexane or pentane and cooled, the precipitate of acid which forms is enriched in E-isomer compared to the starting mixture while the acid remaining in the mother liquor is enriched in Z-isomer compared to the starting mixture. The crystallization temperature may be from 0° to −150°, preferably −20° to −100°. This separation method may be used to obtain E-isomer enriched mixtures from isomer mixtures of these acids of formula (II) wherein $R^1 = H$ and $R^2 = CH_3$ or $—CH_2CH_3$ which have E/Z isomer ratios of 1/1 or larger but preferably at least 2/1. The precipitates of these acids of formula (II) wherein $R^1 = H$ and $R^2 = CH_3$ or $—CH_2CH_3$ which form during the crystallization are mixtures of E- and Z-isomers. The E/Z isomer ratios in these precipitates may be as high as about 50/1.

Separations of E- and Z-isomers of the foregoing acids of formula (II) wherein $R^1 = H$ and $R^2 = CH_3$ and $—C_2H_5$ by crystallization can be applied in many different cases. Among the substrates to which the above crystallization technique may be applied are 3,7-dimethylocta-2,6-dienoic acid, 3,7-dimethyloct-2-enoic acid, 3,7,11-trimethyldodecenoic acid and 3,7-diethylocta-2,6-dienoic acid.

The process of the instant invention allows the preparation of chiral dihydrogeranic acid which can be converted by known methods to menthol, citronellal, citronellol and vitamin E precursor substances having the same chirality as the natural products.

The process of the instant invention is conducted under basic conditions. By reacting in a basic medium, the rate of reaction is increased and the desired positional selectivity and enantioselectivity is insured. Use of rhodium (I) complexes of chiral tertiary phosphines to catalyze hydrogenations of acrylic acids of formula (II) or formula (III) in the absence of base leads to slow, unselective hydrogenations giving undesirable racemic products. The bases that may be used in the instant invention may be selected from alkali metal lower alkoxides, wherein the alkali metals are preferably lithium, sodium and potassium, or amines such as lower alkyl, primary, secondary and tertiary amines. Preferred lower alkyl amines include triethylamine, diisopropylamine, trimethylamine and tributylamine. Cyclic amines such as piperidine may also be used. Inorganic bases such as sodium hydroxide and potassium hydroxide are also usable in the instant invention. The molar ratio of base to the acrylic acid of formula (II) or formula (III) may vary from about 1:1 to about 1:10, preferably from about 1:2 to about 1:5. The hydrogenation may also be carried out on substrates which are preformed alkali metal or ammonium salts of the acids formula (II) or formula (III) as well as reaction mixtures comprising acids of formula (II) or formula (III) and the above-mentioned alkali metal bases or amines. When the hydrogenation is carried out using alkali metal or ammonium salts of formula (II) or formula (III), no additional base is required.

The catalyst utilized herein is a soluble coordination complex of a chiral tertiary phosphine and a rhodium (I) compound.

The source of rhodium is not critical and may be any compound that is convenient. Typical rhodium sources may be selected from $\mu,\mu'$-dichlorobis-[1,5-cyclooctadiene rhodium (I)], hydrated rhodium trichloride, hydrated rhodium tribromide, $(\mu,\mu'$-dichlorobis-[bis-(olefin)rhodium (I)] wherein the olefin may be ethylene, propylene, cyclooctene, etc.; [rhodium (1,5-hexadiene)-Cl]$_2$, [rhodium(bicyclo-2,2,1-hepta-2,5-diene)-Cl]$_2$.

The tertiary chiral phosphines utilized in the instant invention may be selected from the following compounds having the formula:

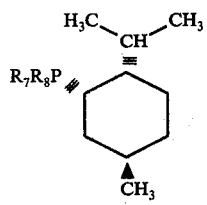

IV wherein $R_7$ is aryl or substituted aryl wherein the substituents are selected from phenyl, tolyl, xylyl, mesityl, phenyl, benzyl, ethylphenyl, cyclohexylphenyl, $R_8$ may be aryl or lower alkyl, wherein said lower alkyl is as previously defined;

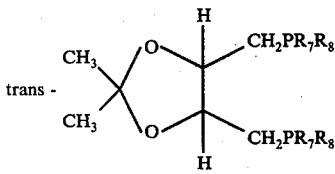

V wherein $R_7$, and $R_8$ are as defined above; when $R_7$ and $R_8$ are both phenyl, the above compound (IV) is designated as chiral trans-4,5-bis-(diphenylphosphinomethyl)2,2-dimethyl-1,3-dioxolane (DIOP):

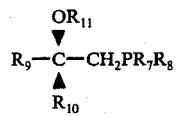

VI

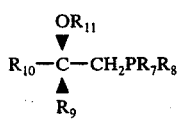

VII wherein $R_7$ and $R_8$ are as defined above, $R_9$ and $R_{10}$ may be aryl or substituted aryl, hydrogen, alkyl hydroxyalkyl, aminoalkyl or perfluoroalkyl, with the proviso that $R_9$ and $R_{10}$ must be different, and $R_{11}$ may be hydrogen, alkyl, aryl or substituted aryl. Among the preferred combinations of $R_9$, $R_{10}$ and $R_{11}$ are:

| $R_9$ | $R_{10}$ | $R_{11}$ |
|---|---|---|
| Phenyl | Hydrogen | Methyl |
| Methyl | Hydrogen | Phenyl |
| Phenyl | Hydrogen | Menthyl |
| Naphthyl | Hydrogen | Methyl |
| 2-Methoxyphenyl | Hydrogen | Methyl |

Among the preferred combinations of $R_7$ and $R_8$ are:

$R_7 = R_8 =$ phenyl
$R_7 = R_8 =$ metal-tolyl
$R_7 = R_8 =$ 3,4-dimethylphenyl
$R_7 = R_8 =$ ortho-methoxyphenyl
$R_7 = CH_3$; $R_8 =$ phenyl
$R_7 =$ isopropyl; $R_8 =$ phenyl.

The phosphines of formula VI and formula VII are novel compounds and form yet another aspect of the instant invention. These novel phosphines are prepared by reacting tetrahydrofuran solutions of the appropriate chiral tosylates with lithium diaryl or arylalkyl phosphides which, in turn, are prepared by known methods.

The molar ratio of tertiary chiral phosphine to the rhodium source which is reacted to form the chiral phosphine rhodium complex catalysts used herein is at least 2:1. Generally, a preferred ratio of P/Rh is about 2:1 to about 10:1, most preferred 2:1 to 4:1. However, if desired, higher ratios of phosphine to rhodium may be utilized. The use of higher ratios, however, provides no additional benefit.

The molar ratio of acrylic acid substrate to catalyst may vary from about 1:1 to about 2000:1 and is preferably about 15:1 to about 2000 to 1 and most preferably about 100 to 1000:1. Ratios greater than 2000:1 may also be used.

Sodium perchlorate has been found to aid in stabilizing the catalyst. Its use, however, is not a critical feature of the instant invention. When used, it is present in an amount of from about 0.01 mole to 0.1 mole, preferably about 0.05 mole per mole of substrate.

The preferred solvents employed in the instant process may be selected from lower alkanols alone or lower alkanols in combination with aromatic hydrocarbons. The lower alkanols are as previously defined. The term "aromatic hydrocarbons" refers to benzene, toluene, xylene and the like, although any inert aromatic hydrocarbon may be used.

In carrying out the instant process, temperature and pressure are not critical. The temperature may range from about $-70°$ C. to about 150° C., preferably from about $-30°$ C. to about 50° C. The pressure may range from about 2 psi to about 500 psi, preferably about 2-100 psi.

The following reaction schemes will serve to generally typify the instant invention:

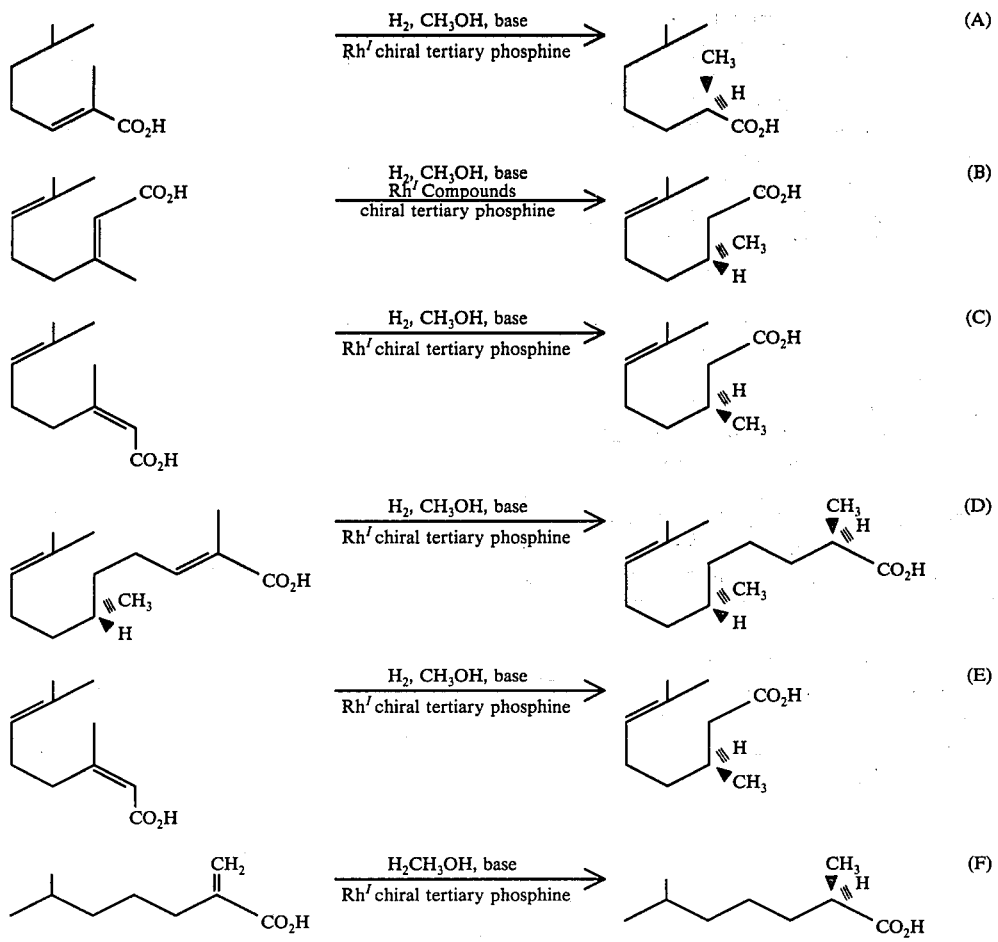

The wedges and broken lines have the significance as described above. It is readily apparent that the chiral tertiary phosphine catalysts used herein form compounds having asymmetric carbon atoms. It can further be realized that the utilization of an acrylic acid derivative high in entgegen content results in compounds having at least a high enantiomeric excess of the R-enantiomer, i.e., at least 50%.

Reactions B, C, D and E illustrate the selectivity aspect of the instant process. In all cases, it is the double bond immediately (point of alpha,beta-unsaturation) adjacent to the carboxyl group that is hydrogenated.

The following non-limiting examples illustrate the process of the instant invention. All ratios are molar ratios unless otherwise stated. The wedges and broken lines have the significance previously described.

The optical purity was calculated in accordance with the following equation;

$$\text{optical purity (in percent)} = \frac{[\alpha]_D^{25} \text{ of sample in 5.0\% CHCl}_3 \text{ solution}}{[\alpha]_D^{25} \text{ of standard in 5.0\% CHCl}_3 \text{ solution}}$$

wherein $[\alpha]_D^{25}$ is the specific rotation of 589 nm ($\text{Na}_D$) radiation produced by sample or standard. Standards used were the pure enantiomers or where the pure enantiomer was unavailable, the standards used were of known optical purity.

The enantiomeric excess was calculated in accordance with the following equation:

$$\text{enantiomeric excess of R-enantiomer (in percent)} = 100 \left( 1 - \frac{2}{\left(1 + \frac{R}{S}\right)} \right)$$

wherein the parameter (R/S) was directly measured by a nmr technique using appropriate chiral shift reagents, for example, EuOptishift II ®[1].

[1] Registered trademark of Willowbrook Laboratories for tris-(perfluoroisopropylcamphorato)europium(III).

Examples 1-5 illustrate the preparation of typical substituted acrylic acids used as substrates in the instant invention.

EXAMPLE 1

Entgegen-2,6-Dimethylhept-2-enoic acid

4-Methylpentanal (18 g.) was added dropwise to a stirred solution of 29.1 g. of carbethoxy methyl methylene triphenyl phosphorane in 100 ml. of methylene chloride. The reaction mixture was stirred overnight, then concentrated on the rotary evaporator. Petroleum ether (50 ml.) was added to precipitate triphenyl phosphine oxide which was removed by filtration and washed with 25 ml. of pentane. The filtrate and washings were combined and concentrated under reduced pressure. The oily residue was distilled through a packed column to yield 13.3 g. (84% yield based on the phosphorane) of ethyl-E-2,6-dimethylhept-2-enoate, b.p. 144°–145° C. (75 mmHg). The ester (0.85 g.) was stirred for 3 hours with 2.5 ml. of methanol and 25 ml. of 1.0 N sodium hydroxide at reflux. The system was allowed to cool, extracted with benzene, made acidic with dilute hydrochloric acid and re-extracted with benzene. The benzene layers were dried over MgSO$_4$, filtered and concentrated under reduced pressure. Kugelrohr distillation gave 0.65 g. (90%) of 2,6-dimethylhept-2-enoic acid, b.p. 102° C. (0.20 mmHg). This procedure gave 2,6-dimethylhept-2-enoic acid which was 96% entgegen isomer according to nmr analysis.

EXAMPLE 2

Entgegen-3,7-Dimethylocta-2,6-dienoic acid

To a mechanically stirred solution of 82 g. (0.482 moles) of silver nitrate in 125 ml. of water was added over a period of 1–2 minutes, a solution of 38.5 g. sodium hydroxide (0.96 moles) in 60 ml. water and 100 ml. methanol. When the resulting precipitate appeared granular and the reaction mixture was at 35°–40° C., 23.3 g. of geranial was added at a rate sufficient to cause the reaction temperature to increase to and remain at 55° C. The reaction mixture was stirred for 45 minutes at 55°–56° C., then cooled and filtered through celite. The solids and the reaction flask were washed with 450 ml. of 2:1 (v/v) methanol/water. The combined washings and filtrate were acidified with 30% sulfuric acid (aqueous) and extracted three times with ether. The combined ether extracts were concentrated under reduced pressure. The crude acid was dissolved in 1N sodium hydroxide and extracted twice with ether. The aqueous layer was then acidified with 10% hydrochloric acid and extracted 3 times with ether. The ether extracts were washed with water, dried over MgSO$_4$ and concentrated under reduced pressure. The crude oil was distilled twice on the Kugelrohr to yield 21.4 g. (83%) of 3,7-dimethylocta-2,6-dienoic acid, b.p. 80° C. (0.05 mmHg). The E/Z ratio of the acid was 13/1 as determined by nmr.

EXAMPLE 3

6R(−)-E-2,6,10-Trimethylundeca-2,9-dienoic acid

A solution of 13.7 g. of 2RS,6R(−)-2,6,10-trimethyl-1,2-epoxy-undeca-3,9-diene in 60 ml. of ether was added to a slurry of magnesium bromide (derived from 800 mg. of magnesium) in 80 ml. of ether at −20° C., stirred for 5 minutes at −20° C. and washed with water. The product was extracted into ether which was exposed for 90 minutes at 25° C. to aqueous methanolic potassium hydroxide (1.4 g. in 50 ml. of 1:1 (v/v) H$_2$O:CH$_3$OH), washed with water, dried and concentrated under reduced pressure. Crude 6R(−)-E-2,6,10-trimethylundeca-2,9-dienal thus obtained was vacuum distilled, b.p. 84°–86° C. (0.5 mmHg); $[\alpha]_D^{25}$ −1.58°.

6R(−)-E-2,6,10-Trimethylundeca-2,9-dienal was converted, by the method of Example 2, to 6R(−)-E-2,6,10-trimethylundeca-2,9-dienoic acid, b.p. 115°–120° C. (0.05 mmHg); $[\alpha]_D^{25}$ −3.41° (c. 2.0, hexane), one pure isomer according to nmr analysis.

EXAMPLE 4

3,7,11-Trimethyldodeca-2,6,10-trienoic acid

Sodium (12 g.) was dissolved in 192 ml. of ethanol and to this solution was added dropwise 60.5 g. of geranylacetone and 102.4 g. of triethylphosphonoacetate in 240 ml. of benzene. The reaction mixture was stirred overnight, then poured over 180 g. of ice and 180 ml. of water. The resulting mixture was extracted twice with 70 ml. of benzene. The organic phases were washed with H$_2$O, dried over MgSO$_4$ and concentrated under reduced pressure. Vacuum distillation gave 66.6 g. (81% yield) of ethyl-3,7,11-trimethyldodeca-2,6,10-trienoate having at C$_2$C$_3$, E/Z ≃ 4.25 and at C$_6$C$_7$, E/Z ≃ 1.5; b.p. 160°–165° C. (0.25 mmHg); 81% yield based on geranyl acetone. This ester was hydrolyzed by the procedure to Example 1 to 3,7,11-trimethyldodeca-2,6,10-trienoic acid having at C$_2$C$_3$E/Z ≃ 3.5 and at C$_6$C$_7$E/Z ≃ 1.5, b.p. 175° C. (1 mm). Yield 46.2 g. (86% based on the ester).

EXAMPLE 5

7RS-3,7,11-Trimethyldodec-2-enoic acid

According to the procedure of Example 4, ethyl-6RS-3,7,11-trimethyldodec-2-enoate having an E/Z = 6.7 was prepared in 74.4% yield from 6RS-6,10-dimethylundecane-2-one and triethylphosphonoacetate. This ester was hydrolyzed, as in Example 4, to make 7RS-3,7,11-trimethyldodec-2-enoic acid having an E/Z = 4.6, b.p. 132° C. (0.057 mmHg) in 91% yield. This sample contained ca. 20 percent of 7RS-3-methylene-7,11-dimethyldodecanoic acid.

EXAMPLE 6

The following example illustrates that 1) 2,6-dimethylheptanoic acid can be prepared from natural citronellal without loss of chirality and 2) that a compound of known optical purity can be used as a standard when an optically pure compound is unavailable.

From 40 gms. of natural citronellal having $[\alpha]_D^{25}$ +14.92° (c. 5.0, CHCl$_3$) was obtained 3R(+)-3,7-dimethyloctan-1-ol. The latter compound was treated with stearoyl chloride and the resulting ester was pyrolyzed as described by Smith and Rouault.[1] The crude distillate (30 ml.) was diluted with benzene (20 ml.), washed neutral with water, dried over MgSO$_4$, concentrated under reduced pressure and vacuum distilled, giving 27.5 g. of distillate.

Smith and Rouault, J. Amer. Chem. Soc. 65, 745 (1943)

This distillate was shown by nmr and gc analysis to consist of ca. 7 parts of the desired 3R(−)-3,7-dimethyl-1-octane and ca. 3 parts of 3,7-dimethyl-2-octene (E/Z ≃ 1.5). This hydrocarbon mixture was oxidized as described by Smith and Rouault, (supra) giving 10.3 g. of product, a mixture of 2R(−)-2,6-dimethylheptanoic acid (~7 parts) and 6-methyl-heptan-2-one (3 parts). This mixture was poured into 1N aqueous sodium hydroxide, extracted with ether to remove the methylheptanone, then acidified with dilute sulfuric acid and again extracted with ether. These ether layers were dried, then concentrated under reduced pressure. Vacuum distillation of the crude product gave 11.8 g. of 2R(−)-2,6-dimethylheptanoic acid as a colorless oil having $[\alpha]_D^{25}$ −13.40° (c. 5.074,CHCl$_3$) and $[\alpha]_D^{25}$ −13.60° (c. 5.029,CHCl$_3$) (two different fractions).

The combined acid fractions were esterified quantitatively with diazomethane to give 2R(−)-methyl-2,6-dimethylheptanoate having $[\alpha]_D^{25}$ −16.61° (c. 1.0895,CHCl$_3$) and $[\alpha]_D^{25}$ −16.5° (c. 1.0245,CHCl$_3$) for two separate distillation fractions.

The ester was subjected to nmr analysis, which showed a R/S ratio of about 7:1, corresponding to ca. 75% enantiomeric excess and also proves that chirality was preserved.

Since citronellal from Java citronella oil has the 3R-configuration, the 2,6-dimethylheptanoic acid obtained therefrom also has the R-configuration. The nmr and optical rotation show that the optical rotation of enantiomerically pure 2R(−)-2,6-dimethylheptanoic acid would have a rotation of ca. −18° and the methyl ester would be ca. −22° (c. 5.0, CHCl$_3$).

EXAMPLE 7

3R(+)-3,7-Dimethyloctanal (obtained from hydrogenation of natural citronellal) was oxidized to 3,7-dimethyloctanoic acid $[\alpha]_D^{25}$ +5.45° (c.2.38 CHCl$_3$) This was esterified via the acid chloride. The methyl ester $[\alpha]_D^{25}$ +4.19° (c. 4.20,CHCl$_3$) was shown by nmr to be 85–90% R-enantiomer (ca. 75% enantiomeric excess). This sample determines the entantiomeric excess of natural citronellal.

The following examples illustrate the enantioselective hydrogenation of alkyl and alkenyl substituted acrylic acid derivatives in accordance with the instant invention.

EXAMPLE 8

Enantioselective hydrogenation of 3,7-dimethylocta-2,6-dienoic acid

A 6 oz. pressure bottle was equipped with a magnetic stirrer, thoroughly purged with argon, and then charged with 20 ml. of methanol, 1.5 g. of 3,7-dimethylocta-2,6-dienoic acid (E/Z≃9), 0.50 g. of NaClO$_4$, 54 mg. of NaOCH$_3$, 98 mg. of neomenthyldiphenylphosphine and 24.5 mg of $\mu,\mu'$-dichloro-bis-[1,5-cyclooctadiene-rhodium (I)]. The system was kept at 0° C. under a pressure of 17 psig of H$_2$ until reaction was complete; a yellow, homogeneous solution was obtained which was then concentrated on the rotary evaporator and distilled under vacuum to give 1.42 g. (95% yield) of 3R(+)-3,7-dimethyloct-6-enoic acid having $[\alpha]_D^{25}$ +6.62° (c. 5.11,CHCL$_3$).

The above product was compared to a sample of 3R(+)-3,7-dimethyloct-6-enoic acid obtained from optically pure pulegone (1-methyl-4-isopropylidene-3-cyclohexanone and which gave $[\alpha]_D^{25}$ +10.19° (c. 5.0,CHCl$_3$), the optical purity of the sample produced by this asymmetric hydrogenation is (6.62/10.19) × 100 = 65%.

The 3R(+)-3,7-dimethyloct-6-enioc acid was converted to its methyl ester using diazomethane, $[\alpha]_D^{25}$ + 4.88° (c. 5.13,CHCl$_3$). The ester was shown by nmr to be a 7:1 mixture of R- and S-enantiomers (ca. 75% e.e.).

EXAMPLE 9

Enantioselective hydrogenation of 3,7-dimethylocta-2,6-dienoic acid

Following the procedure of Example 8, hydrogenation of 3,7-dimethylocta-2,6-dienoic acid (E/Z≃13) at 25° C. with a 3:1 molar P/Rh ratio and 40 psig H$_2$ gave 1.23 g. (82%) of 3R(+)-3,7-dimethyloct-6-enoic acid $[\alpha]_D^{25}$ +6.12° (c. 5.11, CHCl$_3$), which was esterified to give its methyl ester having $[\alpha]_D^{25}$ −4.66° (c. 5.70, CHCl$_3$).

The nmr of the ester showed that the 3R(+) and 3S(−) enantiomers were present in about a 6:1 ratio. The optical purity calculated from the rotation of the acid is 60% and the enantiomeric excess as determined from the nmr of the ester is 71%.

EXAMPLE 10

Enantioselective hydrogenation of 3,7-dimethylocta-2,6-dienoic acid

Following the procedure of Example 8, with the exception of using a substrate/catalyst ratio of 15, the hydrogenation of 3,7-dimethylocta-2,6-dienoic acid (E/Z≃7) was carried out at −23° C. under 130 psig of H$_2$. The reaction was stopped after one week and there was obtained 1.41g. (94% yield) of a mixture of 65% 3,7-dimethyloct-6-enoic acid and 35% 3,7-dimethylocta-2,6-dienoic acid. The rotation of this mixture was $[\alpha]_D^{25}$ +4.59° (c. 5.04, CHCl$_3$) and of the methyl ester was $[\alpha]_D^{25}$ +3.05° (c. 5.08, CHCl$_3$). The nmr of the ester showed a 6:1 ratio of R to S enantiomers in the 3,7-dimethyloct-6-enoic acid. The optical purity calculated from the rotation of the acid is 69%, and the enantiomeric excess determined from the nmr of the ester is 71%.

EXAMPLE 11

Enantioselective hydrogenation of 3,7-dimethylocta-2,6-dienoic acid

Following the procedure of Example 8, the hydrogenation of 3,7-dimethylocta-2,6-dienoic acid (E/Z = 13) was carried out at an initial pressure of 42 psig of H$_2$, at 25° C. with 50 mg. of NaOCH$_3$, in 20 ml. of 1:1 methanol:benzene. 3R(+)-3,7-Dimethyloct-6-enoic acid, 1.35 g. (90%), having $[\alpha]_D^{25}$ +6.25° (c. 5.31, CHCl$_3$) was obtained. The acid was converted to its methyl ester having $[\alpha]_D^{25}$ +4.87° (c. 5.40, CHCl$_3$). The nmr spectra showed a 5:1 ratio of R- and S-enantiomers. The optical purity calculated from the rotation of the acid is 61% and the enantiomeric excess determined from the nmr of the ester is 67%.

EXAMPLE 12

Enantioselective hydrogenation of 3,7-dimethylocta-2,6-dienoic acid

Following the procedure of Example 11, the hydrogenation of 3,7-dimethylocta-2,6-dienoic acid (E/Z = 13) was carried out using 150 mg. of NaOCH$_3$. There was obtained 1.25 g. (83%) of 3R(+)-3,7-dimethyloct-6enoic acid having $[\alpha]_D^{25}$ +6.18° (c. 5.21, CHCl$_3$). The acid was converted to its methyl ester having $[\alpha]_D^{25}$ +4.76° (c. 5.59 CHCl$_3$). The nmr spectra showed a 7:1 ratio of R and S enantiomers. The optical purity is 61% from the rotation of the acid and the enantiomeric excess is 75% as determined from the nmr of the ester.

EXAMPLE 13

Enantioselective hydrogenation of 3,7-dimethylocta-2,6-dienoic acid

Following the procedure of Example 11, the hydrogenation of 3,7-dimethylocta-2,6-dienoic acid was carried out using 250 mg. of NaOCH$_3$. There was obtained 1.33 g. (89%) of 3R(+)-3,7-dimethyloct-6-enoic acid having $[\alpha]_D^{25}$ +6.19° (c. 5.14, CHCl$_3$). The acid was converted to its methyl ester having $[\alpha]_D^{25}$ +4.67° (c. 5.03, CHCl$_3$). The nmr spectra showed a 6:1 ratio of R and S enantiomers. The optical purity from the rotation of the acid is 61% and the enantiomeric excess as determined by the nmr of the ester is 71%.

EXAMPLE 14

Enantioselective hydrogenation of 3,7-dimethylocta-2,6-dienoic acid

Following the procedure and conditions of Example 8, the hydrogenation of 3,7-dimethylocta-2,6-dienoic acid (E/Z = 9) was carried out using 100 ml of piperidine instead of NaOCH$_3$. There was obtained 1.48 g. (99%) of a mixture consisting of 80% of 3R(+)-3,7-dimethyloct-6-enoic acid and 20% of 3R(+)-3,7-dimethyloctanoic acid. This mixture had $[\alpha]_D^{25}$ +6.56° (c. 4.96, CHCl$_3$).

Since a sample of 3R(+)-3,7-dimethyloctanoic acid obtained from pulegone (<99% pure) gave $[\alpha]_D^{25}$ +7.02° (c. 5.03, CHCl$_3$), the rotation for the above mixture of acids is calculated to be +9.55°. This acid mixture was converted to the methyl ester having $[\alpha]_D^{25}$ +4.88° (c. 5.29, CHCl$_3$). The nmr spectra showed a 5:1 ratio of R- and S-enantiomers. The optical purity from the rotation of the acid is 69% and the enantiomeric excess determined from the nmr of the ester is 67%.

EXAMPLE 15

Enantioselective hydrogenation of Z-3,7-dimethylocta-2,6-dienoic acid

Following the procedure of Example 8, hydrogenation of .75 g. of Z-3,7-dimethylocta-2,6-dienoic acid with 250 mg. of NaClO$_4$, 27 mg. of NaOCH$_3$, 49 mg. of neomenthyldiphenylphosphine, and 12.2 mg. of $\mu,\mu'$-dichloro-bis-[1,5-cyclooctadiene-rhodium(I)], in 10 ml. of 1/1 (v/v) methanol/toluene, at 0° C., under an initial pressure of 17 psig of H$_2$ yielded 0.80 g. (100%) of a mixture of 50% starting material and 50% 3,7-dimethyloct-6-enoic acid, having $[\alpha]_D^{25}$ −3.20° C. (c. 5.38, CHCl$_3$). This rotation corresponds to 63% optical purity. The mixture was converted to its methyl ester having $[\alpha]_D^{25}$ −2.62° (c. 5.80, CHCl$_3$). The nmr spectra showed a R/S ratio of 1:8 corresponding to 77% e.e.

EXAMPLE 16

Enantioselective hydrogenation of Z-3,7-dimethylocta-2,6-dienoic acid

Following the procedure of Example 15, hydrogenation of 0.5 g. of Z-3,7-dimethylocta-2,6-dienoic acid with 125 mg. of NaClO$_4$, 50 mg. of NaOCH$_3$, 28.9 mg. of neomenthyldiphenylphosphine, and 7.3 mg. of $\mu,\mu'$-dichloro-bis-[1,5-cyclooctadienerhodium (I)], in 5 ml. of 1/1 (v/v) methanol/toluene, at 24° C., under an initial pressure of 40 psig of H$_2$ yielded 0.41 g. (82%) of a mixture of 70% 3,7-dimethyloct-6-enoic acid and 30% 3,7-dimethyloctanoic acid, having $[\alpha]_D^{25}$ −3.57° (c. 4.99, CHCl$_3$). This rotation indicates ca. 39% optical purity.

EXAMPLE 17

Enantioselective hydrogenation of E-2,6-dimethylhept-2-enoic acid

Using the procedure and conditions of Example 8, hydrogenation of 1.5 g. of E-2,6-dimethylhept-2-enoic acid (E/Z = 96/4) was carried out. There was obtained 1.38 g. (92%) of 2R(−)-2,6-dimethylheptanoic acid having $[\alpha]_D^{25}$ −5.28° (c. 5.06, CHCl$_3$).

In order to determine the optical purity of the acid thus obtained, it was compared to the 2R(−)-2,6-dimethylheptanoic acid prepared in Example 6. Based on the acid of Example 6 (e.e. of 75%), pure 2R(−)-2,6-dimethylheptanoic acid has an optical rotation of $[\alpha]_D^{25}$ −18° (c. 5.0, CHCl$_3$).

Based on the above, the optical purity of the acid produced in this Example is 29%. The acid was then converted to its methyl ester having $[\alpha]_D^{25}$ −6.89° (c. 5.12, CHCl$_3$). Nmr showed a 5:2 ratio of R- and S-enantiomers. The % e.e. as determined by nmr is 43%.

EXAMPLE 18

Enantioselective hydrogenation of E-2,6-dimethylhept-2-enoic acid

Following the procedure of Example 8, and using 20 ml. of methanol, 22 mg. of $\mu,\mu'$-dichloro-bis-[1,5-hexadiene-rhodium (I)], 75 mg. of 4R, 5R-trans-4,5-bis-(di-m-tolylphosphino)-2,2-dimethyl-1,3-dioxolane, and 60 mg. of NaOCH$_3$, 1.0 ml. of E-2,6-dimethylhept-2-enoic acid (E/Z = 96/4) was hydrogenated at 25° C. under an initial pressure of 40 psig of H$_2$. There was obtained 2S(+)-2,6-dimethylheptanoic acid having $[\alpha]_D^{25}$ +3.61° (c. 5.895, CHCl$_3$). The optical purity of the acid is 20%.

EXAMPLE 19

Enantioselective hydrogenation of E-2,6-dimethylhept-2-enoic acid

Following the procedure of Example 8 and using 20 ml. of methanol, 54 g. of NaOCH$_3$, 10 mg. of [bis-(R(+)-o-anisylcyclohexyl-methylphosphine)-(1,5-cyclooctadiene)rhodium (I)]tetrafluoroborate salt, 1.5 g. of E-2,6-dimethylhept-2-enoic acid (E/Z = 96/4) was hydrogenated at 22° C. under an initial pressure of 40 psig of H$_2$. There was obtained 1.22 g. (81%) of 2R(−)-2,6-dimethylheptanoic acid having $[\alpha]_D^{25}$ −5.23° (c. 5.15, CHCl$_3$). The acid was converted to its methyl ester having $[\alpha]_D^{25}$ −6.59° (c. 4.98, CHCl$_3$). NMR showed a 2:1 ratio of R and S enantiomers. The optical purity of the acid is 29% and the enantiomeric excess is 33% as determined from the nmr of the ester.

EXAMPLE 20

Enantioselective hydrogenation of 6R(−)-2,6,10-trimethylundeca-2,9-dienoic acid Following the procedure of Example 8 and using 20 ml. of 1:1 methanol:benzene, 22 mg. of $\mu,\mu'$-dichloro-bis-[1,5-hexadiene-rhodium (I)], 94 mg. of neomenthyldiphenylphosphine, 50 mg. of NaOCH$_3$, entgegen-6R(−)-2,6,10-trimethylundeca-2,9-dienoic acid was hydrogenated at 25° C. under an initial pressure of 40 psig of H$_2$. There was obtained 2R,6R(−)-2,6,10-trimethylundec-9-enoic acid having $[\alpha]_D^{25}$ −3.77° (c 3.74, CHCl$_3$). This was converted to its methyl ester having $[\alpha]_D^{25}$ −4.86° (c 3.38, CHCl$_3$). The nmr of the ester showed a R/S ratio of 2:1, thus indicating 33% e.e.

EXAMPLE 21

Enantioselective hydrogenation of 6R(−)-2,6,10-trimethylundeca-2,9-dienoic acid Following the procedure and conditions of Example 18, but using 25 ml. of methanol and 169 mg. of 4R,5R-trans-4,5-bis-(di-m-tolylphosphino)-2,2-dimethyl-1,3-dioxolane, and 50 mg. of NaOCH$_3$, 1.0 ml. of entgegen-6R(−)-2,6,10-trimethylundeca-2,9-dienoic acid was hydrogenated. There was obtained 0.7 g. of 2S,6R(+)-2,6,10-trimethylundec-9-enoic acid having $[\alpha]_D^{25}$ +1.26° (c. 5.02, CHCl$_3$). The acid was converted to its methyl ester having a $[\alpha]_D^{25}$ +2.31°, (c. 5.07, CHCl$_3$).

The nmr of the ester showed 58:42 R/S ratio of enantiomers, indicating 16% e.e.

EXAMPLE 22

Enantioselective hydrogenation of
6R(−)-2,6,10-trimethylundeca-2,9-dienoic acid

Following the procedure and conditions of Example 21, but using 98 mg. of (+)-(2-phenyl-2-methoxyethyl)-diphenylphosphine, 1.0 ml. of E-6R(−)-2,6,10-trimethylundeca-2,9-dienoic acid was hydrogenated. There was obtained 0.6 g. of a mixture of 60% 2S,6R(+)-2,6,10-trimethylundec-9-enoic acid and 40% 6R(−)-2,6,10-trimethylundeca-2,9-dienoic acid having $[\alpha]_D^{25}$ +0.44° (c 3.88, CHCl$_3$). The acid was converted to its methyl ester having $[\alpha]_D^{25}$ +1.27° (c 5.13 CHCl$_3$). The nmr of the ester showed a 60:40 R/S ratio of enantiomers in the 2S,6R(+)-2,6,10-trimethylundec-9-enoic acid component. This indicates a 20% e.e.

EXAMPLE 23

Enantioselective hydrogenation of
3,7,11-trimethyldodeca-2,6,10-trienoic acid

Following the procedure of Example 8, 1.5 g. of 3,7,11-trimethyldodeca-2,6,10-trienoic acid (at C$_2$C$_3$, E/Z = 3.5; at C$_6$C$_7$, E/Z ≃ 1.5) at 22° C. were hydrogenated. There was obtained 1.35 g. (90%) of a mixture of 3R(+)-3,7,11-trimethyldodeca-6,10-dienoic acid and the more saturated trimethyldodecanoic acids. Nmr of this hydrogenation product showed 33% of the C$_6$C$_7$ bond hydrogenated and 33% of the C$_{10}$C$_{11}$ bond hydrogenated. The mixture had $[\alpha]_D^{25}$ +3.61° (c 5.21, CHCl$_3$). It was converted to its methyl ester having $[\alpha]$ +1.99° (c 5.13, CHCl$_3$).

EXAMPLE 24

Enantioselective hydrogenation of
3,7,11-trimethyldodeca-2,6,10-trienoic acid

Following the procedure of Example 23 but using 97 mg. of (+)-(2-phenyl-2-methoxyethyl)diphenylphosphine, 1.5 g. of 3,7,11-trimethyldodeca-2,6,10-trienoic acid (at C$_2$C$_3$,E/Z = 3.5; at C$_6$C$_7$,E/Z ≃ 1.5) were hydrogenated. There was obtained 1.27 g. (85%) of a 40:60 mixture of starting material and 3S(−)-3,7,11-trimethyldodeca-6,10-dienoic acid. The mixture had $[\alpha]_D^{25}$ −1.91° (c. 5.02, CHCl$_3$). It was converted to its methyl ester having $[\alpha]_D^{25}$ −1.57° (c. 5.10, CHCl$_3$).

EXAMPLE 25

Enantioselective hydrogenation of
7RS-3,7,11-trimethyldodec-2-enoic acid

Following the procedure of Example 23, the hydrogenation of 1.5 g. of 7RS-3,7,11-trimethyldodec-2-enoic acid, (E/Z = 4.5) was carried out. There was obtained 1.48 g. (99%) of 3R(+),7RS-3,7,11-trimethyldodecanoic acid having $[\alpha]_D^{25}$ +4.13° (c. 5.04, CHCl$_3$). The acid was converted to its methyl ester having $[\alpha]_D^{25}$ +1.40° (c 4.14, CHCl$_3$). The nmr of the ester showed a 3:1 ratio of R- and S-enantiomers. The % e.e is therefore 50%.

EXAMPLE 26

Enantioselective hydrogenation of
7RS-3,7,11-trimethyldodec-2-enoic acid

Following the procedure of Example 24, 1.5 g. of 7RS-3,7,11-trimethyldodec-2-enoic acid (E/Z = 4.5) were hydrogenated. There was obtained 0.88 g. (58%) of 3S(−)-3,7,11-trimethyldodecanoic acid having $[\alpha]_D^{25}$ −2.80° (c. 5.00,CHCl$_3$). The acid was converted to its methyl ester having $[\alpha]_D^{25}$ −2.24° (c. 5.27,CHCl$_3$). Nmr showed a 1:2 ratio of R- and S-enantiomers indicating a 33% e.e. of S.

EXAMPLE 27

(+)-(2-Phenyl-2-methoxyethyl)diphenylphosphine (+)-(2-Phenyl-2-methoxyethyl) tosylate (7.6 g., 0.0244 mole) in 25 ml. of tetrahydrofuran was added dropwise at 0° under argon to a rapidly stirred solution of lithium diphenylphosphide (0.0248 mols) in 20 ml. of tetrahydrofuran. The light orange solution remaining after addition was completed and stirred for 10 minutes more, then 25 ml. of deoxygenated brine was added and the resulting mixture was extracted with ether which was dried over Na$_2$CO$_3$, concentrated under reduced pressure and distilled on the Kugelrohr to give (+)-(2-phenyl-2-methoxyethyl)diphenylphosphine as a colorless viscous oil, b.p. 140° (0.02), $[\alpha]_D^{25}$ +44.36° (c. 5.35,CHCl$_3$).

Anal. Calc'd for C$_{21}$H$_{21}$PO: C, 78.73; H, 6.61; P, 9.67. Found: C, 78.65; H, 6.58; P, 9.44

EXAMPLE 28

2-Methylene-6-methylheptanoic acid

In a 35 ml. round bottomed flask connected to a short-path distillation head through a 6 × 1 cm packed column, 10.5 g. (0.06 m.) of 2-hydroxymethyl-6-methylheptanoic acid[(1)] was stirred with 3 drops of phosphoric acid and heated to 170°–180° in vacuum (45 mm.) for 30 minutes. The temperature was then quickly increased to 275° whereupon the product was allowed to distill from the reaction mixture until the head temperature was 155°/45 mm. The distillate, 9.3 g. (98%) was fractioned to give 6.0 g. (64%) of pure 2-methylene-6-methylheptanoic acid, b.p. 123°.

Anal. Calc'd for C$_9$H$_{16}$O$_2$: C, 69.20; H, 10.32. Found: C, 69.41; H, 10.63.

[(1)] Prepared from 6-methylheptanoic acid by the method of P. E. Pfeffer, L. S. Silbert et al., J. Org. Chem., 37, 451, 1256 (1972); ibid, 35, 263 (1970).

EXAMPLES 29–31

Hydrogenations of 2-methylene-6-methylheptanoic acid to 2,6-dimethylheptanoic acid were carried out generally in accordance with Example 34, analysis of the product being carried out following the procedures of Examples 6 and 18. Results are indicated below.

| Ex. No. | Phosphine Used | 2,6-dimethyl-heptanoic acid Rotation | Optical Purity* | Enantiomeric Excess** |
|---|---|---|---|---|
| 29 | Ph$_2$P–(cyclohexyl derivative) | +5.52° | 30 | 30(S) |
| 30 | DIOP | −4.0°(67% hydrogenated) | 32 | 33(R) |
| 31 | H  OCH$_3$  (C$_6$H$_5$)–C–CH$_2$PPh$_2$ | −6.82° | 37 | 39(R) |

*Of the acid in 5.0% CHCl$_3$ solutions.
**By nmr on the methyl ester.

EXAMPLE 32

3,7 Dimethylocta-2,6-dienoic acid (16.4 g., E/Z = 10/1) was dissolved in 150 ml. of distilled hexane, cooled to −78° C., and allowed to stand at that temperature for 2 hours. The fine, white crystals that formed were collected by filtration at −78° C. The crystals were washed out of the funnel with distilled hexane and the resulting solution was concentrated on the rotary. Distillation afforded 9.26 g. of geranic acid (E/Z = 17/1). The filtrate was concentrated to give geranic acid of low E/Z ratio.

EXAMPLE 33

3,7,11-Trimethyldodec-2-enoic acid (3.75 g., E/Z of about 2/1 was dissolved in 25 ml. of n-pentane and the solution was stored 24 hours at −78°. The white, crystalline precipitate was removed by filtration and was distilled to yield 0.91 g. of 3,7,11-trimethyldodec-2-enoic acid of E/Z ratio = 94/6 as determined by nmr. The mother liquors were concentrated and distillation of the residue gave 3,7,11-trimethyldodec-2-enoic acid (2.7 g.) of E/Z ratio of about 3/2, all E/Z ratios being determined by nmr.

EXAMPLE 34

Enantioselective hydrogenation of 3,7-dimethylocta-2,6-dienoic acid

In an inert atmosphere box, under argon atmosphere, a 6 oz. pressure bottle was equipped with a magnetic stirrer and charged with 1 g. of 3,7-dimethylocta-2,6-dienoic acid (E/Z = 17), 10 ml. of methanol, 0.17 g. of $NaClO_4$, 32 mg. of $NaOCH_3$, and 1 ml. of catalyst solution (made by dissolving 241 mg. of neomenthyldiphenylphosphine and 60 mg. of $\mu,\mu$-dichloro-bis-[1,5-cyclooctadiene-rhodium(I)] in enough methanol to make 25 ml. of solution. The system was pressurized with 39 psi of $H_2$ and allowed to stir at room temperature until the theoretical amount of $H_2$ had been consumed. The homogeneous solution was concentrated on the rotary and distilled under reduced pressure to yield 0.80 g. (80%) of a mixture of 93% 3,7-dimethyloct-6-enoic acid and 7% 3,7-dimethylocta-2,6-dienoic acid having $[\alpha]_D^{25} + 6.44°$ (c. 5.02, $CHCl_3$). The acid was converted to its methyl ester having $[\alpha]_D^{25} + 4.81°$ (c. 4.99, $CHCl_3$). The ester was analyzed by nmr as described in Example 7 and shown to be a 4.4:1 ratio of R- and S-enantiomers in the 3,7-dimethyloct-6-enoic acid. The optical purity calculated from the rotation of the acid is 68% [(100/93 × 6.44° ÷ 10.19° = 68)] and the enantiomeric excess determined from the nmr of the ester is 63%.

EXAMPLE 35

Enantioselective hydrogenation of 3,7-dimethylocta-2,6-dienoic acid

Following the procedure described in Example 34, we carried out the hydrogenation of 1 g. of 3,7-dimethylocta-2,6-dienoic acid (E/Z = 17) using 4 ml. of methanol), 0.17 g. of $NaClO_4$, 32 mg. of $NaOCH_3$ and 6 ml. of catalyst solution (made by dissolving 241 mg. of neomenthyldiphenylphosphine and 60 mg. of $\mu,\mu$-dichloro-bis-[1,5-cyclooctadiene-rhodium(I)] in enough methanol to make 25 ml. of solution. We obtained 0.85 g. (85%) of 3,7-dimethyloct-6-enoic acid having $[\alpha]_D^{25} + 5.39°$ (c. 5.01, $CHCl_3$) and was shown by nmr analysis to be a 5.93:1 ratio of R- and S-enantiomers. The optical purity calculated from the rotation of the acid is 67% and the enantiomeric excess determined from the nmr of the ester is 71%.

EXAMPLE 36

Following the procedure of Example 34, the mixture of 1.0 g. of 3,7-dimethylocta-2,6-dienoic acid (E/Z = 17/1), 10 mg. of $NaOCH_3$, 50 mg. of $NaClO_4$ and 16 ml. of a solution prepared to contain 6 mg/ml of a 6:1 molar mixture of neomenthyldiphenylphosphine and [Rh(COD) (Cl)]$_2$ was stirred under 40 psi of hydrogen for 15 days. The product was a 79:21 mixture by nmr of 3,7-dimethyloct-6-enoic acid and unreacted 3,7-dimethylocta-2,6-dienoic acid having a rotation of +5.76° (c. 5.0, $CHCl_3$). Correcting for the optically inactive starting material which remained, the optical purity of the 3,7-dimethylocta-2,6-dienoic acid obtained is 71%.

EXAMPLE 37

(−)-2-Phenoxypropanol $[\alpha]_D^{25} = -38.95°$ (c. 0.9, $CHCl_3$) was treated with tosylchloride in pyridine to give the corresponding (−)-2-phenoxypropyl tosylate of which 1.10 g. was reacted with $LiPPh_2$ following Example 28 to give 0.87 g. of (+)-2-phenoxypropyl diphenylphosphine having $[\alpha]_D^{25} = +27.90°$ (c. 3.03, $CHCl_3$).

Anal. Calc'd for $C_{21}H_{21}OP$: C, 78.73; H, 6.61. Found: C, 78.78; H, 6.31.

EXAMPLE 38

Following generally the procedure of Example 34, 1.2 g. of 3,7-dimethylocta-2,6-dienoic acid with E/Z ≃ 27 was hydrogenated using as catalyst 10 ml. of a solution prepared to deliver 2.0 mg/ml of the catalyst formed from [Rh(1,5-cyclooctadiene) (Cl)]$_2$ and (+)-2-phenoxypropyl diphenylphosphine in 1:6 molar ratio. After 96 hours the reaction was worked up to give 0.95 g. of a ca. 1:1 mixture of 3,7-dimethyloct-6-enoic acid and 3,7-dimethylocta-2,6-dienoic acid. The rotation of this mixture was $[\alpha]_D^{25} = +2.09°$ (c. 4.93, $CHCl_3$) from which the optical purity of the 3,7-dimethyloct-6-enoic acid was calculated to be 38%.

I claim:

1. A chiral phosphine of the formula:

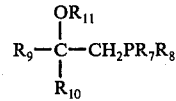

wherein $R_7$ is methyl, isopropyl, xylyl, mesityl, benzyl, aryl or a substituted aryl selected from the group consisting of tolyl, ethylphenyl, cyclohexylphenyl, dimethylphenyl and methoxyphenyl; $R_8$ is lower alkyl, aryl or a substituted aryl selected from the group consisting of tolyl, dimethylphenyl and methoxyphenyl; $R_9$ is hydrogen, alkyl, hydroxylalkyl, aminoalkyl, perfluoroalkyl, aryl or methoxyphenyl; $R_{10}$ is hydrogen, alkyl, aryl, hydroxyalkyl, aminoalkyl or perfluoroalkyl, with the proviso that $R_9$ and $R_{10}$ must be different; $R_{11}$ is hydrogen, alkyl or aryl.

2. The chiral phosphine of claim 1 wherein $R_7$ is phenyl.

3. The chiral phosphine of claim 2 wherein $R_8$ is phenyl.

4. The chiral phosphine of claim 1 wherein $R_9$ is phenyl.

5. The chiral phosphine of claim 1 wherein $R_{10}$ is phenyl.

6. The chiral phosphine of claim 1 wherein $R_{11}$ is phenyl.

7. The chiral phosphine of claim 1 wherein $R_7$ is methoxyphenyl.

8. The chiral phosphine of claim 7 wherein $R_8$ is methoxyphenyl.

9. The chiral phosphine of claim 1 wherein said phosphine is chiral 2-phenyl-2-methoxyethyldiphenyl phosphine.

10. The chiral phosphine of claim 1 wherein said phosphine is chiral 2-phenoxypropyldiphenyl phosphine.

* * * * *